United States Patent [19]

Lackie

[11] Patent Number: 5,152,962
[45] Date of Patent: Oct. 6, 1992

[54] IMMUNOASSAY APPARATUS

[75] Inventor: Steve J. Lackie, Woburn, Mass.

[73] Assignee: ORD Corp., North Salem, N.H.

[21] Appl. No.: 223,154

[22] Filed: Jul. 22, 1988

[51] Int. Cl.[5] .................... G01N 21/00; G01N 21/49
[52] U.S. Cl. .................................. 422/681; 422/58;
 136/800; 136/805; 136/807; 136/172; 356/317;
 250/459.1; 359/15
[58] Field of Search .................. 422/57, 68, 58;
 436/800, 805, 807, 172; 356/317, 318;
 250/459.1, 461.1, 461.2; 350/96.15, 96.18

[56] References Cited

U.S. PATENT DOCUMENTS

| | | | |
|---|---|---|---|
| 4,050,895 | 9/1977 | Hardy et al. | 422/86 |
| 4,133,639 | 1/1979 | Harte | 422/57 |
| 4,257,671 | 3/1981 | Barbaudy et al. | 350/96.18 |
| 4,321,057 | 3/1982 | Buckles | 422/60 |
| 4,399,099 | 8/1983 | Buckles | 436/805 |
| 4,447,546 | 5/1984 | Hirschfeld | 422/57 |
| 4,671,938 | 6/1987 | Cook | 436/805 |
| 4,844,869 | 8/1989 | Glass | 436/805 |

Primary Examiner—James C. Housel
Assistant Examiner—Lyle Alexander
Attorney, Agent, or Firm—Schiller & Kusmer

[57] ABSTRACT

An assay apparatus employing total internal reflection of excitation radiation at the interface between a replaceable optically conductive assay device and a surrounding liquid phase containing the substance being assayed. The assay device is formed of a radiation transmissive, elongated fiber having on the surface thereof a component of a complex formed in an immunological-type specific reaction. A fluorophore that can be excited into fluorescence by the excitation radiation is attached to another component of the complex. The assay device also includes a boss formed of a similarly radiation transmissive material with an index of refraction preferably matched to that of the fiber, one end of the fiber being fixedly coupled to the boss. The boss is dimensioned so that the maximum solid acceptance angle for excitation radiation introduced into the fiber end lies totally within the transmissive medium of said boss. In one embodiment, the fiber is coaxially mounted within a tube that is sized with respect to the fiber so that a fluid sample may be introduced into the tube.

23 Claims, 1 Drawing Sheet

IMMUNOASSAY APPARATUS

This invention relates to optical apparatus for chemical and biochemical assays, and more particularly to an improved fiber optics apparatus for such assays.

It is well known that optical systems employing the principles of attenuated total internal reflection (ATR) spectroscopy are useful in chemical and biochemical analysis or assay. For example, U.S. Pat. No. 4,133,639 discloses a system based on absorption of the evanescent wave by the analyte; U.S. Pat. Nos. 4,321,057 and 4,399,099 both disclose systems that detect changes in the radiation transmitted through the fiber; and U.S. Pat. No. 4,447,546 describes a fluorescence immunoassay system.

In apparatus as described in the aforementioned U.S. Pat. No. 4,447,546 to Hirschfeld, an optical fiber is supported within a capillary tube in approximately concentric alignment therewith. A fluid sample is introduced into the interspace between the fiber and the tube and is drawn into and supported in the interspace by capillary action. To maximize sensitivity and efficiency of such an immunoassay apparatus, it is important that the fiber remain spaced from the internal walls of the capillary tube. If the fiber contacts the capillary wall, capillary action may be adversely affected, and total internal reflection will not be achieved since radiation will leak out of the fiber at the point of contact between the fiber and the capillary wall with attendant loss of sensitivity.

It is important that the end of the fiber into which optical radiation and from which fluorescent radiation are transmitted be supported in a fixed axial position with respect to an optical system for transmitting optical radiation in and out of the fiber. In the event that end of the fiber does not lie at a fixed position with respect to that optical system, the amount and orientation of transmitted radiation entering the fiber may vary, adversely affecting the accuracy and sensitivity of the apparatus.

Several techniques have been developed in known immunoassay apparatus for properly positioning an optical fiber within a capillary tube. The oldest technique involves supporting the proximal end (i.e. the end into which radiation is initially launched) of the optical fiber using a conventional fiber optic connector. Use of these connectors typically involves covering the outer surface of the fiber adjacent its proximal end with a cladding material typically consisting of a transparent high molecular weight polymer. Known cladding materials typically have a refractive index higher than that of the sample, e.g. 1.40 to 1.45, with the result that the numerical aperture of the fiber is reduced to a level at which acceptable sensitivity levels cannot readily be achieved with the apparatus.

Another technique, described in U.S. Pat. No. 4,671,938, involves supporting the fiber in cantilever fashion at its distal end, i.e. the end opposite the end where optical radiation is transmitted into said fiber. The proximal end of an optical fiber supported by this fashion is however displaceable both axially and radially, and such displacement will also cause loss of instrument sensitivity. Further, when the fiber is enclosed in a capillary tube so that a liquid sample being assayed can be introduced into the interspace between the fiber and the capillary tube, the end of the tube surrounding the proximal end of the fiber has not heretofore been readily sealable to prevent leakage of that sample. The toroidal fluid meniscus formed at the end of the tube can serve to prevent fluid flow out of that end of the capillary tube but will, of course, tend to break down when subjected to shock, vibration, high pressure and the like. If the sample being assayed is highly toxic or infectious, such a casual barrier is unacceptable.

In yet another technique for supporting the fiber, the fiber and surrounding capillary tube are disposed in mounting apparatus for attachment to an optical assembly for transmitting excitation radiation into the proximal end of the fiber and receiving fluorescent radiation emitted from the proximal end of the fiber. Included in the apparatus is a mounting assembly for centering the fiber within the capillary tube and for biasing the fiber in a first direction against an annular seat. The latter is designed to support one end of the fiber so that none of the radiation introduced into the fiber is intercepted by the seat.

In such total internal reflection systems, the evanescent zone around the fiber increases in depth and the sensitivity of the system also increases as the numerical aperture of the fiber increases. Also the intensity of the fluorescent signal tunnelling back into the fiber is proportional to a very high power of the numerical aperture (as defined in part by the refractive index of the sample in which fluorescence is excited). Thus, it is preferred that the numerical aperture of the system be maximized, particularly by providing the input radiation at as high a flux as possible over a maximum solid acceptance angle. Such maximization has heretofore been limited by the first of the above-described techniques used to clamp and support the fiber, particularly where the diameter of the fiber employed is very small, e.g. 300-400 microns. To obtain very high numerical apertures using a separate mounting assembly, the art has heretofore typically employed highly corrected lenses with shallow depth of field. Such lenses are expensive, and are difficult to manufacture and to maintain in alignment.

Fiber-optic assay systems having a disposable optical fiber assembly are useful in testing for the presence of harmful viruses. The optical fiber assembly that receives the fluid sample containing the potentially harmful viruses is readily disposable. Thus, to improve the efficiency and reduce the cost of such important and widely-used assay procedures, it is important that the fiber-optic assembly of the assay system be easily replaceable without reducing the desired high numerical aperture.

A principal object of the present invention is therefore to provide an improved fiber-optic assay system that overcomes a number of the above-noted problems of the prior art. Yet another object of the present invention is to provide such an assay system in which an optical wave guide assembly, including an optical fiber or the like, is firmly supported in a fixed relation to an optical system for introducing excitation radiation into the fiber without interference from means for mounting the optical wave guide assembly in the system.

Other objects of the present invention are to provide such a system in which the optical wave guide assembly may be readily inserted into and removed from a mounting frame in which the optics of the system are located, with the assembly being firmly supported and properly optically aligned automatically upon the insertion of the assembly into the base; and to provide such a system in which the desired numerical aperture of the fiber is preserved by supporting the assembly in alignment with the optics of the system such that substantially none of the input optical radiation intersects the mounting frame.

Yet other objects of the present invention are to provide a fiber optic assay system in which the fiber is disposed within a capillary tube and the end of the tube at the proximal end of the fiber can be positively sealed.

Other objects of the present invention will in part be obvious and will in part appear hereinafter.

The foregoing and other objects of the present invention are achieved by a system for assaying a fluid sample, for example with excitation radiation from a radiation source, which radiation is capable of exciting fluorescence in fluorescent material such as a fluorescently tagged antibody/antigen complex. The apparatus comprises a disposable, unitary element in the form of an internally reflecting,-elongated substrate transmissive to both the excitation radiation and to the fluorescence. The unitary element comprises an elongated optical fiber or rod and a plug or boss formed of a similarly radiation transmissive material with an index of refraction preferably matched to that of the fiber. One end of the fiber is fixedly coupled to the boss, the boss being dimensioned so that the maximum solid acceptance angle for excitation radiation introduced into that one end of the fiber through the boss lies totally within the transmissive medium of the boss, the minimum cross-sectional dimension of the boss being thus substantially greater than the cross-sectional dimension of the fiber. The fiber portion of the disposable element may be precoated with at least a moiety of the antibody/antigen complex disposed at least on a portion of the surface thereof.

A preferred embodiment of the present invention also includes a capillary tube disposed in spaced relation about the fiber, the end of the tube adjacent the juncture of fiber and boss being positively sealed to the boss so as to prevent any leakage through that juncture.

One embodiment of the invention includes a mounting frame for rigidly positioning seating means for releasably holding the boss in a fixed position, a source of excitation radiation, optical means for focussing the excitation radiation toward the seating means, and detector means for detecting fluorescence radiation emitted from an end of the fiber responsively to stimulation by the excitation radiation. The mounting frame holds these elements in fixed relation to the seating means so that excitation radiation can be introduced through the boss into the juncture of the fiber and boss within a maximum solid acceptance angle when the boss is properly seated in the seating means.

The invention accordingly comprises the apparatus possessing the construction, combination of elements and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings in which like numerals in the several drawings are employed to denote like parts, and wherein.

Figure 1:
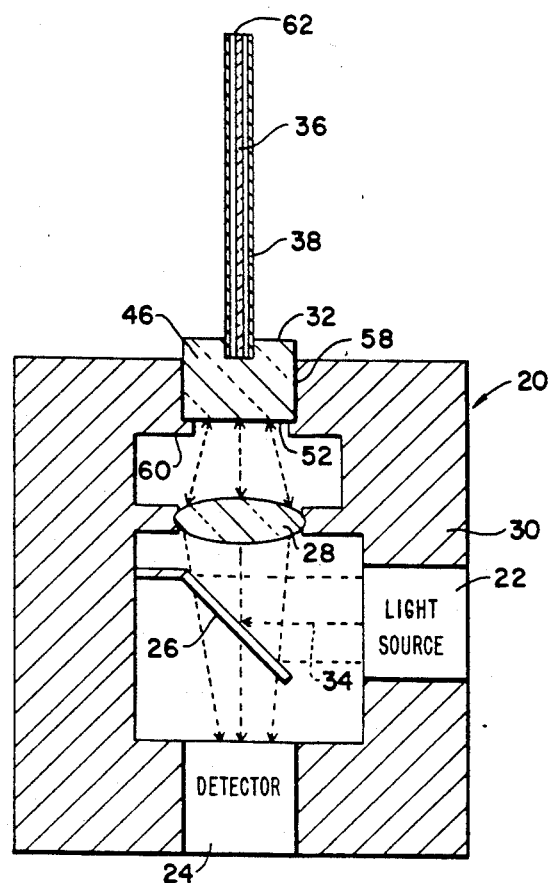
FIG. 1 is a schematic cross-section of assay apparatus incorporating a fiber optic system embodying the principles of the present invention.

In FIG. 1 there is shown exemplary apparatus 20 for assaying a fluid sample, which apparatus incorporates the principles of the present invention. Apparatus 20 comprises an optical system which includes light source 22, light detector 24, a beam splitter such as dichroic or semitransparent mirror 26 and focussing means exemplified by lens 28. The foregoing elements of the optical system are disposed in frame 30 in fixed optical relationship to one another and to assay apparatus 32, as described more fully hereinafter. Thus light beam 36 (shown in broken lines), generated by light source 22 is reflected by mirror 26 so as to pass through lens 28 and into assay apparatus 32.

Figure 2:
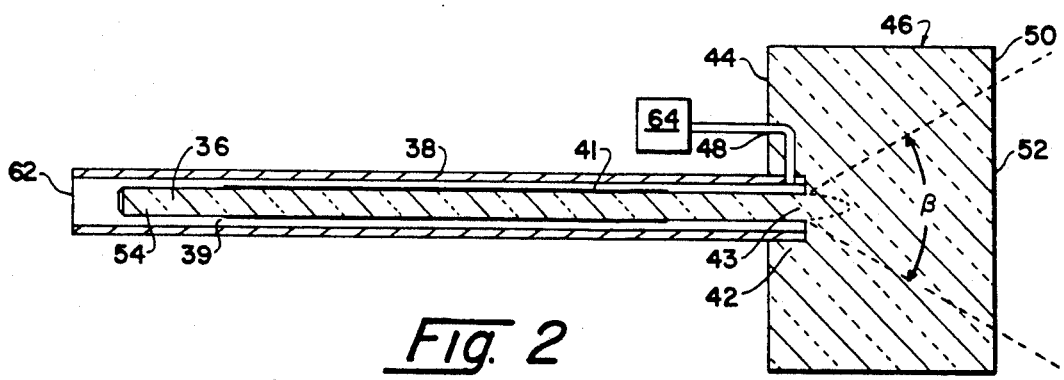
FIG. 2 is an idealized, enlarged, longitudinal cross-section of the fiber optic system of FIG. 1.
Figure 3:
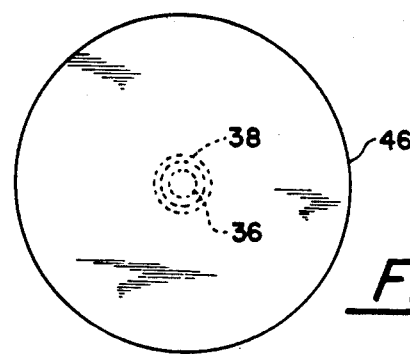
FIG. 3 is a plan view of the proximal face of the system of FIG. 2.

Apparatus 32, shown in detail in FIGS. 2 and 3, includes optical rod or fiber 36 and hollow, elongated enclosure 38, surrounding at least part of fiber 36 and spaced, preferably uniformly from the latter by interspace 39. Fiber 36 is an elongated body substantially transparent to the excitation radiation provided by beam 34 and also transparent to fluorescent radiation excited by the excitation radiation and arising in the evanescent zone around the fiber by virtue of excitation of fluorescent material in that zone. Fiber 36 has a substantially circular cross-section of constant radius although in some embodiments the fiber can be tapered. It is to be understood that the term "fiber" as used herein is intended to include elongated, optically transmissive bodies (e.g. glassy, crystalline and synthetic polymeric materials). For assay purposes, such a fiber is typified by a cylindrical rod having a diameter of 1 mm and a length of about 4 cm, the length and diameter of the rod or fiber being, however, merely exemplary and not to be considered limiting.

Enclosure 38 is preferably, but not necessarily, optically transparent, and is formed of a material that is relatively insoluble and chemically non-reactive with the fluid being assayed. Typically, enclosure 38 is simply a glass or plastic tube having an inside diameter greater than the maximum outside diameter of fiber 36, and preferably dimensioned to delimit a predetermined volume surrounding at least activated coating 41 on fiber 36. Alternatively, enclosure 38 can be a metallic hypodermic needle or other cannula. Interspace 38 between the coated surface of fiber 36 and the inside wall of enclosure 38 is preferably but not necessarily of capillary dimensions. In an exemplary embodiment, it is intended that the operative portion of the surface of fiber 36 be defined by the dimensions of an activated region at which the assay is to be performed. To activate the surface of the operative portion of fiber 36, the latter is typically treated to provide coating 41 such as is described in detail in U.S. Pat. No. 4,447,546 and is incorporated herein by reference.

In apparatus 32, end 43 of fiber 36 is connected, preferably integrally, to the interior surface of central recess 42 in end 44 of a mass of material, shown as plug or boss 46. Recess 42 is provided to permit easy mounting of one end of enclosure 38 in the recess to surround fiber 36. Boss 46 is also formed of a similarly transparent material preferably with an index of refraction matched to that of fiber 36. Alternatively, the index of refraction of boss 46 may be greater than that of the fiber, thus permitting the use of an optical system of lower numerical aperture to achieve the same results.

Preferably but not necessarily, the juncture of fiber 36 and boss 46 represented by end 43 should present no optical discontinuity. To this end fiber 36 and boss 46 can be made by appropriate machining of a single block of glass or plastic, or more practically by an integral molding or casting process, or by inserting one end of an optical fiber into a recess in an appropriately shaped boss and then zone melting the juncture. Alternatively, one can form fiber 36, enclosure 38 and boss 46 as an integral whole as by molding or the like. Boss 46 is in the form of an elongated body preferably coaxially disposed with respect to fiber 36. While typically, the radial cross-section of boss 46 is circular and of substantially constant radius, boss 46 may be provided with a large variety of cross-sectional configurations such as rectangular, triangular, star-shaped, oval and the like and may be tapered or have other non-constant radial dimensions. Where a change in the index of refraction at or adjacent the juncture of fiber 36 and boss 46 is acceptable, the fiber and boss can be formed as separate units and joined together as with an optically appropriate adhesive or by simply drilling a hole of appropriate dimensions in the boss and inserting the fiber in a tight press fit.

Recess 42 typically has a circular cross-section dimensioned so that one end of tubular enclosure 38 can be solidly sealed into recess 42 in fixed concentric relation to fiber 36, frictionally, with adhesive, by melting or the like. Conduit 48 is provided between the surface of end 44 of boss 46 outside the periphery of enclosure 38, and the interior of the latter immediately adjacent the juncture of fiber 36 and boss 46.

Opposite end 50 of boss 46 is shaped to provide surface 52, hereinafter termed the proximal face, typically as a planar surface disposed normally to the longitudinal axis of the fiber 36 and preferably highly polished to minimize any blemishes or surface defects that would tend to scatter incident and emitted radiation. Alternatively, proximal face 52 may be configured in other desired optical shapes to serve, for example, as a magnifying or matching optical surface. For example, with polystyrene (with a typical index of refraction of about 1.6) as the material of a boss and fiber for assaying a sample with an index of refraction typically around 1.34, it would be difficult to use a conventional objective lens system to focus light onto the interface at a proper angle to maintain a high numerical aperture. Hence, it would be highly advantageous to configure proximal face 52 as a lens surface having its optical axis colinear with the axis of elongation of fiber 36 as part of a compound lens system for converting a typically collimated light beam to the correct convergence angle.

Fiber 36 is adapted to propagate along its length, by multiple total internal reflection, optical excitation radiation entering proximal face 52 within a solid conical acceptance angle (B) substantially symmetric with the long axis of the fiber and defined hereinbefore; as well known to those skilled in the fiber optics art. For excitation radiation propagating through an optical fiber of index of refraction $n_o$, and surrounded by a material having an index of refraction of $n_l$, the maximum acceptance angle of input radiation into the fiber is defined as follows:

$$NA = n_2 \sin b = (n_o^2 - n_1^2)^{\frac{1}{2}} \quad (1)$$

where $n_2$ is the refractive index of the medium through which the excitation radiation is originally propagated so as to be incident on an input end of the fiber, and NA is the numerical aperture of the fiber. The maximum acceptance angle B is then:

$$B = \sin^{-1} NA \quad (2)$$

and $B = b$ when $n_2 = 1$ (e.g. $n_2$ is for dry air). The numerical aperture of the fiber is thus higher when the fiber core material has a high index, and the medium surrounding the fiber has a very low index, or $n_o >> n_l$.

Boss 46 is therefore dimensioned both in axial and radial directions so that the solid maximum acceptance angle of excitation radiation introduced into end 43 of fiber 36, lies totally within the medium of boss 46, and the latter therefore has a minimum cross section substantially greater (typically by an order of magnitude or more) than the maximum cross section of fiber 36. The extreme rays of the cone defined as the maximum solid angle of acceptance, as well known in the art, are determined by the index of the sample ($n_l$), the index of refraction of the fiber ($n_o$), and the index of the boss (preferably also $n_l$).

Fiber 36 and plug or boss 46 thus preferably form a unitary or integral form of apparatus 32 and may be any of a very large number of substantially homogeneous materials optically transparent to the excitation radiation, e.g. glassy materials such as glass; crystalline materials such as quartz, sapphire, and the like; synthetic polymers such as polyolefins, polypropylenes, and the like, and is preferably relatively stiff. Where fiber 36 is to be used in fluid assays as described hereinafter, the index of refraction ($n_o$) of the material forming fiber 36 of course must be greater than nl, the index of refraction of the fluid being assayed. The latter index is typically about 1.3 for an aqueous solution. For purposes of an immunoassay apparatus, fiber 36 typically will have a length ranging from 3 cm to 5 cm, with about 4 cm being the preferred length. Fiber 36 generally has a diameter in the range of from about 0.5 mm to 1.5 mm, with about 1 mm being the preferred diameter. It should be understood, however, that such length and diameter are merely exemplary and not limiting.

In a preferred embodiment, in which the fluorescence induced at the surface of fiber 36 by excitation radiation launched down the fiber from proximal face 52 is also collected or observed at face 52, it is desired to prevent stray radiation from going back up the fiber from distal end 54 of fiber 36 to face 52. Consequently, end 54 may be shaped to spill out light incident thereon internally, but preferably is coated with a material matching the index of refraction of the fiber so as to eliminate reflections at the fiber/absorber interface. The absorber material is preferably both non-fluorescent and absorbent with respect to the excitation radiation. The use of an absorber over end 54 also serves to prevent any fluorescence from entering end 54 when the latter is immersed in sample solution. Typically, an epoxy resin loaded with carbon black serves such functions.

In operation of the invention, coating 41 on fiber 36 is formed from any of a number of activating reagents (such as a moiety or constituent of an antibody-antigen complex that includes a fluorescent tag) and is essentially subjected to the same procedures as are described in U.S. Pat. No. 4,447,546. Boss 46 with fiber 36 and tube 38 integrally attached thereto to form apparatus 32 is inserted into aperture 58 in frame 30 until proximal face 52 engages and is fully seated in seat 60 formed in frame 30 at the interior end of aperture 58. To insure that boss 46 will remain releasably seated, biasing means such as leaf springs or the like (not shown) can be provided along the walls of aperture 50 but a friction fit will provide such firm but releasable seating without additional cost or complication. Interspace 39 between enclosure 38 and fiber 36 is filled through unattached end 62 of enclosure 38, as with a hypodermic syringe or other suitable device, with a liquid sample of the material to be assayed. Alternatively, if enclosure 38 is of capillary dimensions, the interspace may easily be filled simply by dipping end 62 into the liquid sample, thus permitting interspace 39 to fill by capillary action. The sample is held in interspace 39 by the surface tension of the liquid evidenced by a meniscus surface formed at end 62 of enclosure 38 and by the capillarity of interspace 39. Filling is expedited by the presence of conduit 48 which permits air to leak out of the interspace as the latter is filled. The sample is allowed to incubate in interspace 39 as desired to permit the material being assayed in the fluid sample to diffuse to and react with coat 41 to form the tagged complex. It will be appreciated that pumping means (shown generally at 64) may be attached to either end of interspace 39 to expedite either filling or emptying the latter, or to provide a flow system that is positively sealed, even against the pressure generated by pumping means 64, at the juncture of the capillary tube and the boss.

Light source 22 is then activated to generate light beam 34, the latter being reflected by mirror 26 so as to fall upon proximal face 52 at less than or equal to the maximum acceptance angle. Lens 28 is selected and axially positioned with respect to seat 60 so that the radially outermost rays of reflected light beam 34 all traverse the medium of boss 46 and pass into fiber 36 just radially inwardly of end 37 at the juncture between the boss and fiber. By this selection and positioning of lens 28, the size of the excitation spot on proximal face 52 and thus on the junction of fiber 36 and boss 46 is precisely controlled. While seat 60 necessarily physically abuts the periphery of aperture 58 it nevertheless never shadows, intercepts or otherwise interferes with the light entering into and emerging from face 52 because the latter is preferably much larger in cross-sectional dimension than the largest light spot on face 52 required to provide the maximum acceptance angle.

As light beam 34 propagates down fiber 36 from face 52, it is capable of exciting or inducing fluorescence in coating 41 by an evanescent wave that accompanies the transmission of the beam down the fiber. A portion of the fluorescence induced in the tagged complex at coat 41 then tunnels back into the fiber from the excited material and is transmitted by total internal reflection back out through proximal face 52, passes through lens 28, through mirror 26 and is focused onto detector 24, thereby indicating the presence of a tagged complex at coat 41. After the assay is completed, the assembly of fiber and boss can be readily removed from its seat in aperture 58 and discarded if desired, leaving the apparatus ready to accept a fresh disposable form of apparatus 32 for a new assay.

It should be observed that the surfaces of fiber 36 other than face 52 are not used for light transmission or for internal reflection, and thus, may be used with impunity for holding, aligning or otherwise positioning apparatus 32 in aperture 58 without interference with the light-guiding properties of assay apparatus 32. Because those surfaces are not used optically, they need not be finished and can bear mold seams, casting marks, metal fittings or the like without impairing transmission characteristics of the apparatus. The relatively large size of boss 46 (compared to the diameter of the fiber) enables apparatus 32 to withstand greater forces than the fiber alone and also permit easy and/or automated handling, again without affecting the transmission characteristics of the apparatus.

The present invention provides fiber optics assay apparatus with as high a numerical aperture as may be achieved subject to the constraints imposed by the refractive index of the sample and the index of the fiber, inasmuch as there is no degradation in numerical aperture due to a contacting, intervening, mounting or cladding material between or at the proximal end of the fiber and that portion of the fiber in which fluorescence is excited. Additionally, since the unitary assembly of fiber 36 and boss 46 is held firmly by assay apparatus 20, there is substantially no loss in throughput that might otherwise occur due to movement of the fiber. Since one may start with a fairly substantial glass "fiber" or rod rather than the fine fibers such as are disclosed in U.S. Pat. No. 4,447,546, one is not limited to the type of glass that may be used, i.e., telecommunication glasses, and therefore one may use, as previously noted, very high index glasses, crystals, polymers, and the like, which further enhance the maximum numerical aperture that can be obtained at the fiber portion in contact with the sample.

The entire surface of boss 46 (other than face 52) and the outside surface of enclosure 38 and end 62 can be provided with a light-tight coating or cover, either as a separate element or as a flowed-on coat. Such a coating would serve to keep stray or room light from the sample area, allowing aperture 58 to be provided in an unprotected area on the outside of the equipment, and thus more accessible for unencumbered replacement and filling. Another advantage of the use of apparatus 32 that incorporates boss 46 is a reduction in bulk fluorescence that is believed to be predominantly caused by scattering in the portion of the fiber between its input face and the area of contact of the fiber surface with the sample fluid. Using boss 46 as the medium through which excitation radiation is launched into the fiber, the section of fiber that provides the scattering is substantially eliminated, thereby reducing the bulk fluorescence.

Since certain changes may be made in the above process and apparatus without departing from the scope of the invention herein involved, it is intended that all matter contained in the above description or shown in the accompanying drawing shall be interpreted in an illustrative and not in a limiting sense.

What is claimed is:

1. Apparatus for assaying a fluid sample with excitation radiation from a radiation source, which radiation is capable of exciting fluorescence in fluorescent material, said apparatus comprising:

a totally internally reflecting, unitary elongated substrate transmissive to both said excitation radiation and to said fluorescence, said substrate comprising a boss and an elongated fiber into one end of which said radiation is to be introduced and at least a portion of the surface of which is adapted to contact said sample;

said one end of said fiber being fixedly coupled to said boss, said boss being dimensioned so that the maximum solid acceptance angle for said excitation radiation introduced into said one end lies totally within the transmissive medium of said boss.

2. Apparatus as defined in claim 1 wherein the juncture of said fiber and boss presents no optical discontinuity to propagation of said radiation down said fiber.

3. Apparatus as defined in claim 1 wherein said boss has an index of refraction matched to that of said fiber.

4. Apparatus as defined in claim 1 including a coating of said fluorescent material on at least a portion of the surface of said fiber.

5. Apparatus as defined in claim 4 where said fluorescent material includes at least a moiety of an antibody-antigen complex that includes a tag that will provide said fluorescence when excited by an evanescent wave generated by said excitation radiation.

6. Apparatus as defined in claim 1 including a hollow elongated enclosure disposed about and spaced from said fiber so as to provide an interspace between said fiber and said enclosure.

7. Apparatus as defined in claim 6 wherein said fiber is disposed concentrically within said enclosure.

8. Apparatus as defined in claim 6 wherein the interspace between said enclosure and said fiber is of capillary dimensions.

9. Apparatus as defined in claim 6 wherein one end of said elongated enclosure abuts and is substantially sealed to said boss adjacent the juncture of said fiber and said boss.

10. Apparatus as defined in claim 9 including conduit means extending between the exterior of said apparatus and the interspace between said enclosure and said fiber adjacent said boss.

11. Apparatus as defined in claim 1 including pumping means so connected to said interspace as to provide a fluid-sealed system for flowing said sample through said interspace.

12. Apparatus as defined in claim 1 including means associated with the other end of said fiber for blocking propagation of excitation and fluorescent radiation and stray light through said other end.

13. In apparatus as defined in claim 12 wherein said means for blocking comprises a radiation absorber having an index of refraction substantially matched to the index of refraction of said fiber.

14. Apparatus as defined in claim 1 wherein the surface of said boss opposite the juncture of said boss and fiber is substantially planar and disposed substantially perpendicularly to the axis of elongation of said fiber.

15. Apparatus as defined in claim 1 wherein the surface of said boss opposite the juncture of said boss and fiber is configured to provide a lens surface, the optical axis of which is substantially colinear with the axis of elongation of said fiber.

16. Apparatus as defined in claim 1 wherein the minimum cross-sectional dimension of said boss transverse to the axis of elongation of said fiber is substantially greater than the maximum cross-sectional diameter of said fiber.

17. Apparatus as defined in claim 1 including:
seating means for holding said boss in a fixed position;
a source of said excitation radiation;
optical means for focussing said radiation toward said seating means;
detector means for detecting fluorescence radiation emitted from an end of said fiber responsively to said excitation radiation; and
means for mounting said source, optical means and detector means in fixed relation to said seating means for introducing said excitation radiation into said end of said fiber through said boss within said acceptance angle when said boss is held in said seating means.

18. Apparatus as defined in claim 17 including:
beam splitting means coupled to said means for mounting so as to direct said excitation radiation to said optical means and for directing said fluorescence to said detector means.

19. Apparatus as defined in claim 17 wherein said boss includes a substantially planar face substantially perpendicular to the longitudinal axis of said fiber and lying on a surface of said boss opposite to the juncture of said fiber and said boss.

20. Apparatus as defined in claim 17 wherein the surface of said boss opposite the juncture of said boss and fiber is configured to provide a lens surface, the optical axis of which is substantially colinear with the axis of elongation of said fiber.

21. Apparatus as defined in claim 17 wherein said boss has a cross-sectional configuration substantially matched to the shape of said seating means so that said boss can be firmly and releasably held in said seating means.

22. Apparatus as defined in claim 17 wherein said boss has a circular cross-section and a substantially uniform diameter 23. Apparatus as defined in claim 17 including pumping means so connected to said interspace as to provide a fluid-sealed system for flowing said sample through said interspace.

* * * * *